United States Patent
Beech, Jr. et al.

[11] Patent Number: 5,942,651
[45] Date of Patent: Aug. 24, 1999

[54] PROCESS FOR CONVERTING $C_9+$ AROMATIC HYDROCARBONS TO LIGHTER AROMATIC PRODUCTS BY TRANSALKYLATION IN THE PRESCENCE OF TWO ZEOLITE-CONTAINING CATALYSTS

[75] Inventors: James H. Beech, Jr., Wilmington, Del.; Stuart Damon Hellring, Yardley; Terry Eugene Helton, Glen Mills, both of Pa.; Timothy Frederick Kinn, Humble, Tex.; Sadi Mizrahi, Cherry Hill, N.J.; Norman J. Rouleau, Yardley, Pa.

[73] Assignee: Mobile Oil Corporation, Fairfax, Va.

[21] Appl. No.: 08/874,875

[22] Filed: Jun. 13, 1997

[51] Int. Cl.$^6$ ...................................................... C07C 5/22
[52] U.S. Cl. ........................................... 585/475; 585/470
[58] Field of Search ...................................... 585/475, 470

[56] References Cited

U.S. PATENT DOCUMENTS

| | | | |
|---|---|---|---|
| 3,308,069 | 3/1967 | Wadlinger et al. | 252/455 |
| 3,702,886 | 11/1972 | Argauer et al. | 423/328 |
| 3,729,409 | 4/1973 | Chen | 208/135 |
| 3,767,568 | 10/1973 | Chen | 208/134 |
| 3,832,449 | 8/1974 | Rosinski et al. | 423/328 |
| 3,948,758 | 4/1976 | Bonacci et al. | 208/92 |
| 3,957,621 | 5/1976 | Bonacci et al. | 208/60 |
| 3,965,208 | 6/1976 | Butter et al. | 260/671 M |
| 3,965,209 | 6/1976 | Butter et al. | 260/671 M |
| 4,001,346 | 1/1977 | Chu | 260/671 M |
| 4,007,231 | 2/1977 | Butter | 260/672 T |
| 4,011,276 | 3/1977 | Chu | 260/672 T |
| 4,016,218 | 4/1977 | Haag et al. | 260/671 R |
| 4,016,219 | 4/1977 | Kaeding | 260/672 T |
| 4,029,716 | 6/1977 | Kaeding | 260/672 T |
| 4,052,476 | 10/1977 | Morrison | 260/672 T |
| 4,100,215 | 7/1978 | Chen | 260/671 M |
| 4,117,026 | 9/1978 | Haag et al. | 260/671 R |
| 4,127,471 | 11/1978 | Suggitt et al. | 208/60 |
| 4,150,062 | 4/1979 | Garwood et al. | 260/671 R |
| 4,152,364 | 5/1979 | Chu | 585/454 |
| 4,365,104 | 12/1982 | Kaeding | 585/467 |

(List continued on next page.)

OTHER PUBLICATIONS

Das et al., "Transalkylation and Disproportionation of Toluene and $C_9$ Aromatics over Zeolite Beta" 23 Catalyst Letters pp. 166–168 (1994).

Das et al., "Zeolite Beta Catalyzed $C_7$ and $C_9$ Aromatics Transformation" 116 Applied Catalysis A:Genreal, pp. 71–79 (1994).

Wang et al., "Disproportionation of Tolunes and of Trimethylbenzene and Their Transalkylation over Zeolite Beta", 29 Ind. Eng. Chem. Res. pp. 2005–2012 (1990).

Yamada et al. "Hydrogenation by $CoMo/Al_2O_3$ Catalyst (Part 3) Effect of $H_2S$ on Hydrogenation of Monoaromatic Hydrocarbons" vol. 31, No. 2, Sekiyu Gakkaishi, pp. 118–124 (1988).

*Primary Examiner*—Glenn Caldarola
*Assistant Examiner*—Thuan D. Dang
*Attorney, Agent, or Firm*—Peter W. Roberts; Malcolm D. Keen

[57] ABSTRACT

A process for converting a heavy aromatics feed to lighter aromatic products, such as benzene and xylene, by reacting $C_{9+}$ aromatic hydrocarbons and toluene or benzene under transalkylation reaction conditions, over a first catalyst composition including a zeolite having a constraint index ranging from 0.5 to 3 and a hydrogenation component and a second catalyst composition including an intermediate pore size zeolite having a constraint index ranging from 3 to 12 and a silica to alumina ratio of at least about 5, to produce a transalkylation reaction product containing benzene or toluene and xylene. The benzene or toluene from the reaction product can then be distilled to obtain a benzene or toluene product.

8 Claims, 1 Drawing Sheet

U.S. PATENT DOCUMENTS

| | | | |
|---|---|---|---|
| 4,367,359 | 1/1983 | Kaeding | 585/467 |
| 4,370,508 | 1/1983 | Kaeking | 585/467 |
| 4,380,685 | 4/1983 | Chu | 585/466 |
| 4,418,235 | 11/1983 | Haag et al. | 585/407 |
| 4,439,409 | 3/1984 | Puppe et al. | 423/328 |
| 4,753,720 | 6/1988 | Morrison | 208/135 |
| 4,812,223 | 3/1989 | Hickey, Jr. et al. | 208/111 |
| 4,857,666 | 8/1989 | Barger et al. | 585/323 |
| 4,891,458 | 1/1990 | Innes et al. | 585/323 |
| 4,954,325 | 9/1990 | Rubin et al. | 423/328 |
| 5,030,787 | 7/1991 | Absil et al. | 585/475 |
| 5,406,016 | 4/1995 | Cook et al. | 585/475 |

PROCESS FOR CONVERTING C₉+ AROMATIC HYDROCARBONS TO LIGHTER AROMATIC PRODUCTS BY TRANSALKYLATION IN THE PRESCENCE OF TWO ZEOLITE-CONTAINING CATALYSTS

FIELD OF THE INVENTION

The invention relates to the conversion of heavy aromatics, specifically $C_9+$ aromatics, to lighter aromatic products. More particularly, the invention relates to the production of benzene having an improved purity level.

BACKGROUND OF THE INVENTION

A source of benzene and xylene is catalytic reformate, which is prepared by mixing petroleum naphtha with hydrogen and contacting the mixture with a strong hydrogenation/dehydrogenation catalyst, such as platinum, on a moderately acidic support, such as a halogen-treated alumina. Usually, a $C_6$ to $C_8$ fraction is separated from the reformate, extracted with a solvent selective for aromatics or aliphatics to separate these two kinds of compounds and to produce a mixture of aromatic compounds that is relatively free of aliphatics. This mixture of aromatic compounds usually contains benzene, toluene and xylenes (BTX), along with ethyl benzene.

Refineries have also focused on the production of benzene and xylene by transalkylation of $C_9+$ aromatics and toluene over noble metal-containing zeolite catalysts. During the transalkylation of $C_9+$ aromatics and toluene to high value petrochemical products, such as benzene and xylene, over catalysts containing noble metals, by-product saturate compounds are typically produced during the first several months on stream. These by-product saturate compounds, referred to as coboilers, can boil in the same temperature range as a high value petrochemical product, making separation of the high value petrochemical product at high purity levels difficult. For example, a benzene product for commercial sale must exceed 99.85% purity. However, initial benzene product purity after distillation of a transalkylation reaction product is typically only about 99.2% to 99.5% due to the presence of coboilers, such as methylcyclopentane, cyclohexane, 2,3-dimethylpentane, dimethylcyclopentane and 3-methylhexane. Therefore, an additional extraction step is usually required to further improve benzene product purity to the desired level.

In view of the difficulty in obtaining a high purity benzene petrochemical product due to the presence of coboilers that are formed during the transalkylation of $C_9+$ aromatics and toluene over noble metal-containing zeolite catalysts, it is desirable to reduce the level of coboilers that is produced in the transalkylation reaction. An advantage of reducing the level of coboilers that is produced in the transalkylation reaction is that a high purity benzene product may be obtained after distillation of the transalkylation reaction product, without the need for an additional extraction step, thereby reducing the number of steps that is required to obtain a benzene product having a purity of at least 99.85%.

SUMMARY OF THE INVENTION

The present invention is generally directed to a method for converting heavy aromatics to lighter aromatic products. More particularly, the present invention is directed to a method for reducing the level of coboilers that is produced during the transalkylation of heavy aromatics, specifically $C_9+$ aromatics, and toluene to benzene and xylene.

The invention is directed to a process for converting a feed comprising $C_9+$ aromatic hydrocarbons and toluene to a product comprising benzene and xylene, wherein the process comprises the step of contacting a feed comprising $C_9+$ aromatic hydrocarbons and toluene under transalkylation reaction conditions with (1) a first catalyst composition comprising a zeolite having a constraint index ranging from 0.5 to 3 and a hydrogenation component, and (2) a second catalyst composition comprising an intermediate pore size zeolite having a constraint index ranging from 3 to 12 and a silica to alumina ratio of at least about 5, to produce a transalkylation reaction product comprising benzene and xylene. A benzene product having a purity of at least 99.85% may be obtained by distilling the benzene from the transalkylation reaction product, without the need for an extraction step.

DETAILED DESCRIPTION OF THE INVENTION

Figure 1:
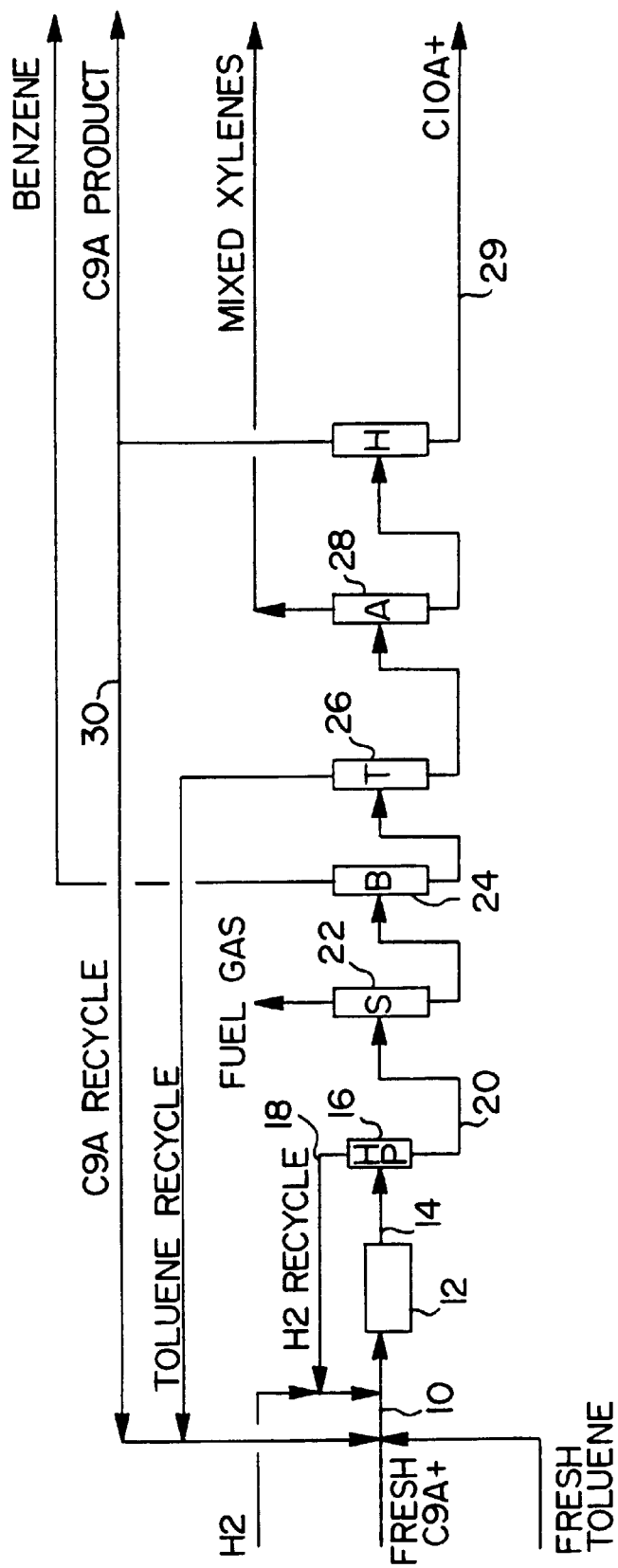
FIG. 1 shows a typical process flow scheme for the transalkylation process.

The present invention is generally directed to a method for converting heavy aromatics to lighter aromatic products.

More particularly, the present invention is directed to a method for reducing the level of coboilers that is produced during the transalkylation of heavy aromatics, specifically $C_9+$ aromatics, and toluene to benzene and xylene, to produce a transalkylation reaction product comprising benzene and xylene. A benzene product having a purity of at least 99.85% may be obtained by distilling the benzene from the transalkylation reaction product, without the need for an extraction step.

A feature of the invention that achieves the production of high purity benzene resides in the reduction or elimination of the production of coboilers in the transalkylation of heavy aromatics and toluene to benzene and xylene, by use of a first catalyst composition comprising a zeolite having a constraint index ranging from 0.5 to 3 and a hydrogenation component and a second catalyst composition comprising an intermediate pore size zeolite having a constraint index ranging from 3 to 12 and a silica to alumina ratio of at least about 5. The method by which the constraint index of a zeolite is determined is described fully in U.S. Pat. No. 4,016,218, the entire contents of which are hereby incorporated by reference.

An advantage in the reduction or elimination of coboilers in the transalkylation of heavy aromatics and toluene to benzene and xylene is the elimination of an extraction step, which is ordinarily required to obtain high purity benzene.

First Catalyst Composition

The reaction of this invention is catalyzed by contact with a first catalyst composition comprising a zeolite having a constraint index of 0.5 to 3. Zeolites that are especially useful include zeolites MCM-22, PSH-3, SSZ-25, ZSM-12 and zeolite beta.

Zeolite beta is more particularly described in U.S. Pat. No. Re. 28,341 (of original U.S. Pat. No. 3,308,069), the entire contents of which are hereby incorporated by reference.

ZSM-12 is more particularly described in U.S. Pat. No. 3,832,449, the entire contents of which are hereby incorporated by reference.

SSZ-25 is described in U.S. Pat. No. 4,954,325, the entire contents of which are hereby incorporated by reference.

PSH-3 is described in U.S. Pat. No. 4,439,409, the entire contents of which are hereby incorporated by reference.

Zeolite MCM-22, or simply "MCM-22", is more particularly described in U.S. Pat. No. 4,954,325, the entire contents of which are hereby incorporated by reference.

It may be desirable to incorporate the zeolite with another material that is resistant to the temperatures and other conditions employed in the process of this invention. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

Use of a material in conjunction with the zeolite, i.e. combined therewith or present during its synthesis, which itself is catalytically active, may change the conversion and/or selectivity of the catalyst composition. Inactive materials suitably serve as diluents to control the amount of conversion so that transalkylated products can be obtained economically and orderly without employing other means for controlling the rate of reaction. These catalytically active or inactive materials may be incorporated into, for example, naturally occurring clays, e.g. bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with the zeolite herein as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolite can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

The zeolite is usually admixed with the binder or matrix material so that the final catalyst composition contains the binder or matrix material in an amount ranging from about 5 to 90 weight %, and preferably from about 10 to 60 weight %.

The zeolite of the first catalyst composition is employed in combination with at least one hydrogenation component, such as a metal selected from Group VIII of the Periodic Table of the Elements (CAS version, 1979). Specific examples of useful hydrogenation components are iron, ruthenium, osmium, nickel, cobalt, rhodium, iridium, or a noble metal such as platinum or palladium.

The amount of the hydrogenation component is selected according to a balance between hydrogenation activity and catalytic functionality. Less of the hydrogenation component is required when the most active metals such as platinum are used as compared to palladium, which does not possess such strong hydrogenation activity. Generally, less than 10 weight % is used and often not more than 1 weight %.

The hydrogenation component can be incorporated into the first catalyst composition by co-crystallization, exchanged into the composition to the extent a Group IIIA element, e.g., aluminum, is in the structure, impregnated therein, or mixed with the zeolite and a binder. Such component can be impregnated in or on the zeolite, for example in the case of platinum, by treating the zeolite with a solution containing a platinum metal-containing ion. Suitable platinum compounds for impregnating the catalyst with platinum include chloroplatinic acid, platinous chloride and various compounds containing platinum amine complex, such as $Pt(NH_3)_4Cl_2 \cdot H_2O$.

Alternatively, a compound of the hydrogenation component may be added to the zeolite when it is being composited with a binder, or after the zeolite and binder have been formed into particles by extrusion or pellitizing.

After treatment with the hydrogenation component, the catalyst composition is usually dried by heating the catalyst composition at a temperature of about 150° to 320° F., and more preferably about 230° to 290° F., for at least about 1 minute and generally not longer than about 24 hours, at pressures ranging from about 0 to 15 psia. Thereafter, the catalyst composition is calcined in a stream of dry gas, such as air or nitrogen, at temperatures of from about 500° to 1200° F. for about 1 to 20 hours. Calcination is preferably conducted at pressures ranging from about 15 to 30 psia.

Prior to use, steam treatment of the catalyst composition may be employed to minimize the aromatic hydrogenation activity of the catalyst composition. In the steaming process, the catalyst composition is usually contacted with from about 5 to 100% steam, at a temperature of at least about 500° to 1200° F. for at least about one hour, specifically about 1 to 20 hours, at a pressure of about 14 to 360 psia.

Second Catalyst Composition

The second catalyst composition of the present invention comprises an intermediate pore size zeolite having a constraint index ranging from 3 to 12 and a silica to alumina ratio of at least about 5. A zeolite that is particularly useful includes ZSM-5, as described in U.S. Pat. No. 3,702,886, the entire contents of which are hereby incorporated by reference, or the proton or hydrogen form thereof, namely HZSM-5. The zeolite of the second catalyst composition is capable of converting undesired $C_6$ and $C_7$ non-aromatics over relatively short contact times of about 1 minute or more, and preferably about 2 minutes or more.

The zeolite of the second catalyst composition may be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

The zeolite is usually admixed with the binder or matrix material so that the final catalyst composition contains the binder or matrix material in an amount ranging from about 5 to 90 weight %, and preferably from about 10 to 60 weight %.

The second catalyst composition may consitute from about 1 to 20 weight %, and preferably from about 10 to 15 weight % based on the total weight of the first and second catalyst compositions in the transalkylation reactor zone. For example, the second catalyst composition may be substituted for a portion of the first catalyst composition at the bottom of the reactor, whereby the first catalyst composition resides in a first catalyst bed and the second catalyst composition resides in a second catalyst bed in the same reactor. Alternatively, the first catalyst composition may reside in a first reactor and the second catalyst composition may reside in a second reactor. Thus, in one embodiment of the invention, where the catalysts are contained in two different beds, $C_{9+}$ aromatic hydrocarbons and toluene or benzene are reacted under transalkylation conditions over the first catalyst bed comprising the first catalyst composition as described above to produce an intermediate product stream and the intermediate product stream is then passed over the second catalyst bed comprising the second catalyst composition as described above to produce a final transalkylation reaction product comprising benzene or toluene and xylene.

The Feed

The $C_9+$ aromatics used in this process will usually comprise one or more aromatic compounds containing at least 9 carbon atoms such as, e.g. trimethylbenzenes, dimethylbenzenes, and diethylbenzenes, etc. Specific $C_9+$ aromatic compounds include mesitylene (1,3,5-trimethylbenzene), durene (1,2,4,5-tetramethylbenzene), hemimellitene (1,2,4-trimethylbenzene), pseudocumene (1,2,4-trimethylbenzene), 1,2-methylethylbenzene, 1,3-methylethylbenzene, 1,4-methylethylbenzene, propyl-substituted benzenes, butyl-substituted benzenes, isomers of dimethyl-ethylbenzenes, etc.

Suitable sources of the $C_9+$ aromatics is any $C_9+$ fraction from any refinery process that is rich in aromatics. This aromatics fraction contains a substantial proportion of $C_9+$ aromatics, e.g., at least 80 weight % $C_9+$ aromatics, wherein preferably at least about 80 weight %, and more preferably more than about 90 weight %, of the hydrocarbons will range from $C_9$ to $C_{12}$. Typical refinery fractions which may be useful include catalytic reformate, FCC naphtha or TCC naphtha.

A source of toluene may be from an aromatics extraction plant or any commercial source.

Typically, the feed to the transalkylation reaction zone comprises the $C_9+$ aromatics and toluene. The feed may also include recycled/unreacted toluene and $C_9+$ aromatics that is obtained by distillation of the effluent product of the transalkylation reaction itself. Typically, toluene constitutes from about 40 to 90 weight %, and preferably from about 50 to 70 weight % of the entire feed. The $C_9+$ aromatics constitutes from about 10 to 60 weight %, and preferably from about 30 to 50 weight % of the entire feed to the transalkylation reaction zone.

Hydrocarbon Conversion Process

The process can be conducted in any appropriate reactor including a radial flow, fixed bed, continuous down flow or fluid bed reactor. The transalkylation reaction temperature typically ranges from about 650° to 950° F., and preferably from about 750° to 850° F.; the pressure from about 100 to 600 psig, and preferably from about 200 to 500 psig; the hydrogen to hydrocarbon molar ratio from about 1 to 5, and preferably from about 1 to 3. The charge rate over the first catalyst composition ranges from about 1.0 to 7.0 WHSV, and preferably from about 2.5 to 4.5 WHSV; and the charge rate over the second catalsyt composition ranges from about 5.0 to 100.0 WHSV, and preferably from about 15.0 to 35.0 WHSV. The transalkylation reaction conditions are sufficient to convert a heavy aromatic feed to a product containing substantial quantities of $C_6$–$C_8$ aromatic compounds, such as benzene, toluene and xylenes, especially benzene and xylene.

Referring to FIG. 1, a simplified process flow scheme is illustrated. The $C_9+$ aromatics stream along with toluene and hydrogen are introduced via line 10 to reactor 12 which contains the first and second catalyst compositions. The reactor is maintained under conditions sufficient so that toluene and methyl aromatics (toluene, xylenes, trimethylbenzenes and tetramethylbenzenes) approach thermodynamic equilibrium through transalkylation. The product of reactor 12 is withdrawn via line 14 and introduced to a hydrogen separator 16 which separates hydrogen for recycle to reactor 12 via line 18. The feed then passes via line 20 to a stabilizer section 22 that removes $C_5$- fuel gas by known techniques. Thereafter, the product is fractionated into benzene, toluene and xylenes streams in fractionators 24, 26 and 28, respectively, for separation of these streams. The remaining product which comprises unreacted $C_9+$ feed and any heavy aromatics is separated into a $C_9$ aromatics stream 30 and a $C_{10}+$ aromatics stream 29. Stream 30 is recycled back to the reactor feed, removed from the process, or a combination of both (partial recycle). The $C_{10}+$ aromatics stream 29 is suitable for gasoline blending or other product such as solvents.

What is claimed is:

1. A process for converting $C_9+$ aromatic hydrocarbons to lighter aromatic products, comprising the step of reacting (i) the $C_9+$ aromatic hydrocarbons and (ii) toluene or benzene under transalkylation reaction conditions, over a first catalyst composition comprising a zeolite having a constraint index ranging from 0.5 to 3 and a hydrogenation component and a second catalyst composition comprising an intermediate pore size zeolite having a constraint index ranging from 3 to 12 and a silica to alumina ratio of at least about 5, to produce a transalkylation reaction product comprising (i) benzene or toluene and (ii) xylene.

2. A process for producing benzene comprising the steps of:
    (a) reacting (i) $C_9+$ aromatic hydrocarbons and (ii) toluene or benzene under transalkylation reaction conditions, over a first catalyst composition comprising a zeolite having a constraint index ranging from 0.5 to 3 and a hydrogenation component and a second catalyst composition comprising an intermediate pore size zeolite having a constraint index ranging from 3 to 12 and a silica to alumina ratio of at least about 5, to produce a product stream comprising (i) benzene or toluene and (ii) xylene; and
    (b) distilling the benzene or toluene from said product stream to obtain a benzene or toluene product.

3. The process according to claim 2, wherein the benzene product of step (b) has a purity of at least 99.85%.

4. The process according to claim 3, wherein the benzene product of step (b) has a purity of at least 99.85%, without the need for an additional extraction step.

5. The process according to claim 1, wherein the hydrogenation component of the first catalyst composition is at least one metal selected from Group VIII of the Periodic Table of the Elements and the zeolite of the first catalyst composition is selected from the group consisting of MCM-22, PSH-3, SSZ-25, ZSM-12 and zeolite beta.

6. The process according to claim 5, wherein the zeolite of the second catalyst composition is ZSM-5.

7. The process according to claim 1, wherein the transalkylation reaction conditions comprise a temperature ranging from about 650° F. to 950° F., a pressure ranging from about 100 to 600 psig, and a hydrogen to hydrocarbon mole ratio ranging from about 1 to 5.

8. A process for converting $C_9+$ aromatic hydrocarbons to lighter aromatic products, comprising the steps of (a) reacting (i) the $C_9+$ aromatic hydrocarbons and (ii) toluene or benzene under transalkylation reaction conditions, over a first catalyst bed comprising a first catalyst composition that comprises a zeolite having a constraint index of 0.5 to 3 and a hydrogenation component to produce an intermediate product stream, and (b) passing said intermediate product stream over a second catalyst bed comprising a second catalyst composition that comprises an intermediate pore size zeolite having a constraint index ranging from 3 to 12 and a silica to alumina ratio of at least about 5, to produce a final transalkylation reaction product comprising (i) benzene or toluene and (ii) xylene.

\* \* \* \* \*

UNITED STATES PATENT AND TRADEMARK OFFICE
CERTIFICATE OF CORRECTION

PATENT NO. : 5,942,651
DATED : August 24, 1999
INVENTOR(S) : James H. Beech, et al.

It is certified that error appears in the above-identified patent and that said Letters Patent is hereby corrected as shown below:

"Mobile Oil Corporation" should read ---Mobil Oil Corporation---.

Signed and Sealed this
Fourth Day of January, 2000

Attest:

Attesting Officer

*Acting Commissioner of Patents and Trademarks*